United States Patent [19]

Hirata et al.

[11] Patent Number: 5,714,646
[45] Date of Patent: Feb. 3, 1998

[54] PROCESS FOR PRODUCING ISOPROPYL ALCOHOL

[75] Inventors: Shigeru Hirata; Shinji Ogawa, both of Yokohama, Japan

[73] Assignee: Mitsui Toatsu Chemicals, Inc., Tokyo, Japan

[21] Appl. No.: 568,294

[22] Filed: Dec. 6, 1995

[30] Foreign Application Priority Data

Dec. 15, 1994 [JP] Japan ................... 6-311812
Dec. 15, 1994 [JP] Japan ................... 6-311813

[51] Int. Cl.$^6$ .................... C07C 29/04; B01D 3/42
[52] U.S. Cl. .................... 568/899; 203/28; 568/895
[58] Field of Search ................ 203/2, 3, 14, 18, 203/DIG. 16, 28; 568/899, 889, 895

[56] References Cited

U.S. PATENT DOCUMENTS

| | | | |
|---|---|---|---|
| 3,994,983 | 11/1976 | Webers et al. | |
| 4,234,748 | 11/1980 | Frampton et al. | 568/901 |
| 4,340,769 | 7/1982 | Brandes et al. | 568/899 |
| 4,357,147 | 11/1982 | Bezman | 568/899 |
| 4,482,767 | 11/1984 | Imai | 568/899 |
| 4,484,013 | 11/1984 | Schmidt | 568/899 |
| 4,507,512 | 3/1985 | Okumura et al. | 568/897 |
| 4,861,923 | 8/1989 | Olah | 568/899 |

FOREIGN PATENT DOCUMENTS 60-24082  6/1985  Japan.
60-149536 8/1985  Japan.

OTHER PUBLICATIONS

Esteban A. Brignole et al, "Supercritical Fluid Extraction of Alcohols from Water", *Ind. Eng. Chem. Res.*, 1987, 26, pp. 254–261.

*Primary Examiner*—Virginia Manoharan
*Attorney, Agent, or Firm*—Burns, Doane, Swecker & Mathis

[57] ABSTRACT

A process for producing isopropyl alcohol by hydrating directly propylene and water in the presence of a strong acid solid catalyst which includes feeding continuously propylene, water which is the same as or more than propylene in terms of mole, and a saturated hydrocarbon (propane, butane and the like) to a reactor in which the above solid catalyst is filled or suspended, and carrying out a hydration reaction in the conditions of 50° to 200° C. and 60 to 250 atm while maintaining the concentration of isopropyl alcohol contained in the reaction liquid at 6 to 30 weight %, and then drawing a vapor phase out of the reactor, liquefying a part of thereof by reducing the pressure or cooling to separate vapor components, and refining crude isopropyl alcohol contained in the liquid phase to obtain refined isopropyl alcohol.

8 Claims, 1 Drawing Sheet

５,714,646

1

PROCESS FOR PRODUCING ISOPROPYL ALCOHOL

BACKGROUND OF THE INVENTION (1) Field of the Invention

The present invention relates to a process for producing isopropyl alcohol, which is industrially used as a solvent for paint, a medicine, an agricultural chemical, a synthetic raw material and a detergent, by direct hydration of propylene.

(2) Description of the Related Art

The production of isopropyl alcohol by liquid phase direct hydration of propylene has been known for a long time as well as the production of sec-butanol by hydration of butene. A catalyst used for the hydration reaction is an acid catalyst, and a production process making use of a strong acid cation exchange resin or heteropolyacid is industrialized.

Above all, in a process using a solid catalyst represented by a strong acid cation exchange resin, the hydration reaction is carried out under the conditions of low temperature and low pressure such as 100° to 150° C. and 60 to 250 atm as compared with the case where a heteropolyacid is used, and such conditions are advantageous for constructing the reactor or the reaction system.

Since a great part of isopropyl alcohol is industrially used in an anhydrous form, a low concentration alcohol aqueous solution obtained at the outlet of a reactor in such liquid phase direct hydration process has to be concentrated to an anhydrous condition. Since isopropyl alcohol forms a minimum boiling point azeotropic mixture with water, isopropyl alcohol is usually produced as an anhydrous product by a rectification operation after subjecting the aqueous solution to azeotropic distillation and dehydration distillation, and therefore energy needed for such concentration is quite enormous.

In order to reduce such concentration energy, a process is proposed in which a hydration reaction is carried out under a supercritical condition or a subcritical condition of olefin used for the hydration reaction to distribute the resulting alcohol in an olefin vapor phase.

A process for producing almost anhydrous sec-butanol is described in Japanese Patent Laid-Open No. 60-149536, wherein in producing sec-butanol from n-butene and water using liquid phase heteropolyacid as a catalyst, a liquid phase hydration reaction is carried out under the conditions of temperature and pressure exceeding the critical temperature and the critical pressure of n-butene, respectively; the reaction mixture present in a vapor phase is drawn out of a reactor in a gaseous phase, and cooled and liquefied to separate an oil phase from water; and unreacted n-butene is removed from the separated oil phase. This process is a good example in which an azeotropic operation is not required and energy needed for concentration has been seemingly reduced to a large extent. However, this process has the industrial problem that the conversion of raw material butene is confined to about 10%, and therefore not only an expanded reactor volume is required, but also the large amount of unreacted butane of nine times or more as much as the theoretical amount needed for the production of alcohol is required to be circulated to the inlet of the reactor to reuse it.

Further, described in Japanese Patent Publication No. 60-24082 is a process characterized in that in subjecting vaporized lower olefin having a carbon number of 2 to 6 to direct catalytic hydration with liquid water in the presence of a strong acidic solid at high temperatures and high pressures and separating the resulting aqueous crude alcohol from the reaction product to thereby obtain lower alcohol having a carbon number of 2 to 6, (1) an olefin-containing vapor stream is introduced into a reactor filled with an acid catalyst from the bottom thereof, and at least one mole of liquid water per mole of the olefin to be reacted is charged into the reactor; (2) the reaction is carried out at temperature and pressure conditions which are higher or at least slightly lower than the critical temperature and critical pressure of olefin; (3) the whole aqueous phase of the reaction mixture is left in the reactor or the major amount thereof is returned to the reactor; (4) a vapor stream containing unreacted olefin and almost all the reaction product is discharged from the top of the reactor; and (5) crude products mainly comprising the resulting alcohol is separated from the discharged vapor stream in a liquid state. It is reported that according to this process, the selectivity of the resulting isopropyl alcohol is high and isopropyl alcohol separated in a liquid state is obtained in a high concentration. Further, it is reported that the high selectivity relates to the fact that almost all the reaction products are transferred directly into the vapor phase and an alcohol concentration in the liquid phase is maintained extremely low. According to the disclosure in the examples, a liquid phase hydration reaction is carried out at 100 atm and 135° C.; the selectivity of isopropyl alcohol is 99% or more, and 80% of the separated liquid is alcohol; and a high concentration is achieved.

In this process, however, the present inventors have found that the azeotropic composition of 88 wt % (68 mole %) of isopropyl alcohol has not yet been reached. Further, with respect to the reaction conversion, propylene of a fresh raw material is fed in an amount of 5.6 mole per hour to obtain 4.2 moles of isopropyl alcohol after separating a liquid phase, and the overall conversion comes up to 75%. It is obvious, however, that since a part of the vapor coming out of the outlet of the reactor which contains unreacted olefin, is circulated to the reactor to reuse it, the one pass yield between the inlet and the outlet of the reactor is 75% or less, though the yield is not clarified.

Further, according to the knowledge and the analysis of the present inventors, it has been clarified that in the hydration reaction, by the process described in Japanese Patent Publication No. 60-24082 the propylene conversion at the outlet of the reactor is confined to about 8% in the conditions of 135° C. and 100 atm, when the concentration of isopropyl alcohol contained in the liquid phase is maintained extremely low, for example, 10 wt % or less as described in the above publication. That is, the process of the above publication does not provide the high yield of isopropyl alcohol until a part of the vapor at the outlet of the reactor is circulated directly to the reactor to be reused. This increases considerably the volume of the reactor, and it still remains unchanged that the circulated amount of unreacted olefin can not help becoming large. Accordingly, it can be said that the direct solution of the industrial problems have not yet been attained.

SUMMARY OF THE INVENTION

An object of the present invention is to provide a production process in which in producing isopropyl alcohol by direct hydration of propylene in the liquid phase, isopropyl alcohol of a high concentration is produced in a reactor at a high conversion and in which the energy needed for concentration is reduced and a large reactor volume is not required.

According to one aspect of the present invention, provided is a process for producing isopropyl alcohol by hydrating directly propylene and water in the presence of a strong acid solid catalyst, separating a crude alcohol aqueous solution from the reaction products thus obtained, and subjecting the above aqueous solution to refining treatment. The process comprises:

(1) supplying continuously propylene, water corresponding to at least 1 mole or more per mole of propylene to be reacted, and a saturated hydrocarbon to a reactor in which the above solid catalyst is filled or suspended, (2) carrying out a hydration reaction while maintaining both of the temperature and the pressure of the inside of the reactor to be not lower or slightly lower than the critical temperatures and the critical pressures of the above propylene and hydrocarbon, (3) circulating the whole amount or a part of a liquid phase out of the resulting reaction products to the inlet of the reactor in such a flow amount that water contained in the above liquid phase accounts for 10 mole or more per mole of propylene to be reacted, and (4) drawing the whole amount of a vapor phase out of the reaction products from the reactor together with unreacted materials and the saturated hydrocarbon, liquefying isopropyl alcohol and water by reducing the pressure and cooling to separate vapor components, and refining thus obtained crude isopropyl alcohol contained in the above liquefied phase to obtain refined isopropyl alcohol.

According to another aspect of the present invention, the following processes are provided:

the process described above, wherein the amount of the saturated hydrocarbon fed is 4 to 200 mole % based on the amount of propylene fed;

the process described above, wherein the amount of the saturated hydrocarbon fed is 10 to 200 mole % based on the amount of propylene fed;

the process described above, wherein unreacted propylene and the saturated hydrocarbon are recovered from the whole amount or a part of non-condensed vapor by distillation and circulated to the inlet of the reactor;

the process described above, wherein a hydration reaction is carried out while maintaining the concentrations of isopropyl alcohol in the liquid phases at 6 weight % or more at least at the inlet and the outlet of the reactor; and the process described above, wherein the concentrations of isopropyl alcohol in the liquid phases at the inlet and the outlet of the reactor are controlled by any of (1) circulating the whole amount or a part of the liquid phase out of the reaction products to the inlet of the reactor in such a flow rate that water contained in the above liquid phase accounts for 10 moles or more per mole of propylene fed, (2) leaving the whole amount or the major part of the liquid phase in the reactor, or (3) supplying isopropyl alcohol to the inlet of the reactor or the circulated liquid phase.

DESCRIPTION OF THE PREFERRED EMBODIMENTS

Figure 1:
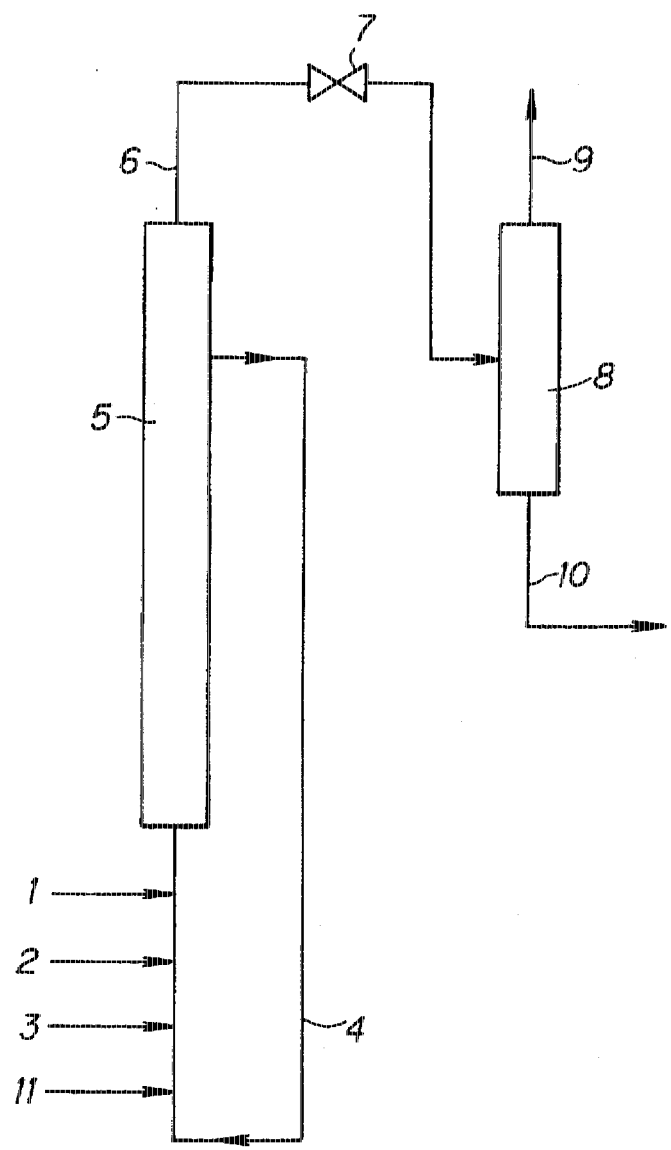
FIG. 1 is a flow sheet for effectuating the process of the present invention.

In the flow sheet of FIG. 1, 1 is propylene feed pipe; 2 is a water feed pipe; 3 is a saturated hydrocarbon fee pipe; 4 is a liquid phase-circulating pipe; 5 is a reactor; 6 is vapor phase-discharging pipe; 7 is a pressure controlling valve; 8 is a vapor-liquid separator; 9 is a hydrocarbon discharging pipe; 10 is a condensed liquid phase-discharging pipe; and 11 is an isopropyl alcohol feed pipe.

The strong acid solid catalyst intended in the present invention is not specifically restricted, and any catalysts having strong acid functional groups, particularly strong acid cation exchange resins can Suitably be used. The above solid catalyst may be filled in a reactor in the form of a fixed bed or may be used in a suspension. Catalysts having solubility in water such as liquid phase heteropolyacid can be used as well, but such catalysts necessitate the use of acid resistant high grade construction materials having, for example, hastelloy and titanium for a reactor and auxiliary facilities in many Cases because of corrosiveness thereof, and therefore solid catalysts are preferably used in terms of production facilities.

It is known that a process in which alcohol formed by a liquid phase hydration reaction of an olefin is recovered in an unreacted olefin vapor phase provides a high concentration of alcohol recovered after separating the olefin as compared with that of alcohol recovered from a liquid phase in which the concentration is restricted by a reaction equilibrium. In order to reduce energy needed for the concentration of this recovered alcohol, it is requested that the amount of isopropyl alcohol distributed in the olefin vapor phase is sufficiently greater than that of water similarly distributed. Further, in order to enhance the conversion of olefin in a reactor, that is, the ratio of the amount of alcohol recovered in the olefin vapor phase to the amount of olefin fed to the reactor, it is requested that the amount of alcohol distributed into the olefin vapor phase is large.

Investigations made by the present inventors from such point of view as described above have resulted in finding that isopropyl alcohol can be selectively distributed in a large quantity from a liquid phase into a saturated hydrocarbon vapor phase wherein a saturated hydrocarbon has a carbon number of 1 to 6, preferably 2 to 5 and more preferably 3 to 4, by using the saturated hydrocarbon in the conditions of the temperature and the pressure which exceed or are slightly lower than its critical temperature and critical pressure. A hydrocarbon having too small a carbon number reduces isopropyl alcohol-extracting ability, and one having too large a number causes the above temperature to deviate from the temperature at which hydration is carried out. The examples of particularly preferred hydrocarbons include propane, n-butane, and i-butane. Surprisingly, the present inventors have found that comparison in the same pressure and temperature conditions reveals that the distributed amount of isopropyl alcohol in these saturated hydrocarbons is very large as compared with the case where an unsaturated hydrocarbon such as propylene is used. It is the new discovery by the present inventors that when a saturated hydrocarbon or an unsaturated hydrocarbon is used, such a large difference between the distributed amounts of isopropyl alcohol exists, and such phenomenon has not so far been known at all.

According to the vapor liquid equilibrium data of a three-components system of isopropyl alcohol-water-hydrocarbon measured by the present inventors, when propane, which is a saturated hydrocarbon, is used in the conditions exceeding the critical temperatures and critical pressures of both of propylene (critical temperature: 365° K. (92° C.) and critical pressure: 4.61 Mpa (46 atm)) and propane (critical temperature: 369.7° K. (96.7° C.) and critical pressure: 4.25 MPa (42 atm)), for example, in the conditions of 393° K. (120° C.) and and 8.1 MPa (80 atm), the amount of isopropyl alcohol present in a saturated hydrocarbon vapor phase comes up to about 2.5 times as much as the case where propylene is used. In addition, the present inventors have found that the hydrocarbon-free concentration of isopropyl alcohol contained in the hydrocarbon vapor phase reaches about 75 mole % (91 wt %) in the case of propane while being about 65 mole % (86 wt %) in the case of propylene. This concentration (75 mole %) exceeds even 68 mole % (88 wt %) in the azeotropic composition of isopropyl alcohol and water. Further, it has become clear that when n-butane (critical temperature: 425.6° K. (152.6° C.) and critical pressure: 3.76 MPa (37 atm)) is used in the same temperature and pressure conditions, the amount of isopropyl alcohol present in the hydrocarbon vapor phase comes up to about 3 times as much as in the case where propylene is used and that the hydrocarbon-free concentration of isopropyl alcohol also exceeds 70 mole %.

Use of such a saturated hydrocarbon as prescribed in the present invention, for example, a saturated hydrocarbon having a carbon number of 3 to 4 together with propylene in a propylene hydration reactor in the temperature and pressure conditions exceeding or slightly lower than the critical temperature and critical pressure thereof makes it possible to distribute selectively isopropyl alcohol formed by liquid phase hydration of propylene into the hydrocarbon vapor phase in a large quantity, and this provides advantageous effects, which are unobvious and can not be estimated by a person having an ordinary skill in the art. This invention can achieve a reduction in energy consumption for concentration of isopropyl alcohol and a greater propylene conversion as described above.

The reaction conditions of the temperature and the pressure in the reactor in which a hydration reaction is carried out preferably exceed the critical pressures of propylene and the saturated hydrocarbon used, and in addition, more preferably exceed the critical temperatures thereof. The higher hydration reaction temperature is advantageous from the viewpoint of the reaction rate. Too high temperature reduces the concentration of isopropyl alcohol distributed in the hydrocarbon vapor phase and is disadvantageous from the viewpoint of a reduction in energy consumption for concentration. When the reaction temperature is too low, the amount of isopropyl alcohol distributed in the hydrocarbon vapor phase is lowered, and the propylene conversion is reduced as well. The hydration reaction is carried out preferably in a range of 50° to 200° C., more preferably 80° to 150° C.

In the present invention, propylene, water and a saturated hydrocarbon is continuously supplied to the reactor filled with a solid catalyst to carry out the hydration reaction. As already described, propane, n-butane and/or iso-butane can be preferably used as the saturated hydrocarbon which is caused to coexist with propylene. These hydrocarbons are allowed to coexist singly with propylene or may be used in combination. Among them, propane is preferably used as the saturated hydrocarbon since it is generally contained in raw material propylene. Thus, for process design, it is reasonable to use propane as the saturated hydrocarbon because it is contained in raw material propylene.

The amount of the saturated hydrocarbon used has no specific critical restriction. As this amount is increased, the propylene conversion can be enhanced. However, energy consumed to feed or circulate the hydrocarbon increases as well. Accordingly, the coexisting amount is at least 4 to 200 mole %, preferably 10 to 200 mole %, and more preferably 10 to 100 mole % based on the amount of propylene fed to the reactor. Water is fed in an amount of at least 1 mole or more (as new charge) per mole of propylene to be reacted. The upper limit thereof is not specifically restricted and is 30 moles or less, preferably 5 moles or less.

In the present invention, the hydrocarbon vapor phase in the reactor is mainly composed of unreacted propylene, a saturated hydrocarbon, isopropyl alcohol, water, and by-produced diisopropyl ether. Propane may coexist as well depending on raw material propylene, and the amount of unreacted propylene can be markedly reduced by adjusting the coexisting amount of the saturated hydrocarbon. After discharging continuously such hydrocarbon vapor phase as described above from the reactor, the vapor is subjected to reducing the pressure to below the critical pressures of propylene and the saturated hydrocarbon and, if necessary, cooling to below the critical temperatures, whereby isopropyl alcohol and water are liquefied into a condensed liquid phase and are separated from unreacted gaseous propylene and the saturated hydrocarbon.

Thus, an isopropyl alcohol aqueous solution of a high concentration equivalent to or more than 68 mole %, which is an azeotropic composition, can be obtained. According to the present invention, since an azeotropic distillation is substantially not needed and in addition, the amount of coexisting water is reduced, energy needed for concentration is greatly reduced.

In the present invention, gaseous unreacted propylene and the saturated hydrocarbon are recovered by conventional distillation after being separated from the isopropyl alcohol, and circulated again to the reactor, whereby all of them can be used. Needless to say, in the case where unreacted propylene and the saturated hydrocarbon are accompanied with a very small amount of isopropyl alcohol, it is effective for improving a raw material consumption that isopropyl alcohol is recovered from the bottom of the distillation column and fed to a refining step.

In the present invention, the whole amount or the major part of the liquid phase containing water as a principal component in the reactor can be left in the reactor. More preferably, it is preferred from the viewpoint of reaction selectivity in the liquid phase hydration reaction and the removal of heat of reaction to draw out continuously the whole amount or the major part thereof from the outlet of the reactor and to circulate it to the inlet of the reactor for reuse. The circulating flow rate of the liquid phase is preferably maintained in such an amount that the amount of water in the circulating liquid is 10 moles or more per mole of propylene to be reacted in the reactor. More preferably, the circulating flow rate of the liquid phase is controlled so that the amount of water is 10 moles or more per mole of propylene to be fed to the reactor. Thus, the by-produced amount of diisopropyl ether in the hydration reaction can be reduced. In FIG. 1, propylene, water and a saturated hydrocarbon are designed to be supplied to a liquid phase circulating line, but it will be naturally obvious to a person having an ordinary skill in the art that they may be fed to the reactor.

However, isopropyl alcohol which is thus separated from propylene and the saturated hydrocarbon and has a high concentration equivalent to or more than that of an azeotropic composition contains a little amount of water. A drying operation is preferably carried out in order to obtain an anhydrous alcohol. Conventional processes such as drying by azeotropic distillation with benzene, toluene or hexane and drying with desiccants such as zeolite can be applied.

The preferred embodiment of the present invention is that the hydration reaction is carried out while maintaining the concentration of isopropyl alcohol in the liquid phase at 6 weight % or more at least at the inlet and the outlet of the reactor.

It is preferable to carry out the above reaction that the concentration of isopropyl alcohol in the liquid phase at the inlet and the outlet of the reactor is controlled by supplying isopropyl alcohol to the inlet of the reactor or the circulated liquid phase.

The process of the present invention is clearly different from prior techniques in that a prescribed considerable amount of isopropyl alcohol may be caused to coexist in advance in water continuously fed to the hydration reaction. To be more concrete, the present invention is distinctly different from Japanese Patent Publication No. 60-24082 (page 4, the seventh column, lines 40 to 42) in which the concentration of isopropyl alcohol in a liquid phase is maintained extremely low, in that a prescribed amount or more of isopropyl alcohol is caused to be preferably present together with water in any parts of the liquid phase in the reactor, in combination with that the whole amount or the major part of the liquid phase reaction products at the outlet of the reactor is circulated to the inlet of the reactor.

According to a new discovery made by the present inventors, in a process in which substantially almost all of isopropyl alcohol to be a reaction product of propylene is drawn out of a reactor in the form of a vapor phase, the conversion of propylene is closely related to the concentration of isopropyl alcohol in the liquid phase. In the conditions that the reaction temperature and the reaction pressure are the same, the higher the concentration of alcohol is, the higher the conversion of propylene to isopropyl alcohol drawn out as a vapor phase is. The distribution equilibrium of a solute (isopropyl alcohol) contained in an aqueous phase to such supercritical or subcritical olefin has not so far been known at all. For example, if the concentration of isopropyl alcohol in the liquid phase is 25 weight %, a propylene conversion of 20 can be achieved at a reaction temperature of 130° C. and a reaction pressure of 120 atm when well-known strong acid cation exchange resins are used as a catalyst. It should be recognized that this has achieved a notable improvement while the olefin conversions in Japanese Patent Publication No. 60-24082 and Japanese Patent Laid-Open No. 60-149536 are 10% at most.

In this case, a liquid phase at the inlet of the reactor is a mixture of at least two of newly supplied water, isopropyl alcohol which may be newly supplied together with water and a liquid phase circulated from the outlet of the reactor. A preferred embodiment of the present invention is that the concentration of isopropyl alcohol contained in the liquid phase at the inlet of the reactor is controlled by the amount of isopropyl alcohol newly supplied together with water so that the concentration becomes substantially almost the same as the one of isopropyl alcohol contained in the liquid phase circulated from the outlet of the reactor.

In the present invention, it is preferred in terms of enhancing the propylene conversion that the concentration of isopropyl alcohol which coexists with water is sufficiently high. However, too high a concentration thereof increases the by-production rate of diisopropyl ether and is not suitable for the process. The concentration of isopropyl alcohol in the liquid phase is preferably 6 to 30 weight %, preferably 10 to 25 weight % in terms of an improvement in the conversion and a reduction in ether by-production.

EXAMPLES

The present invention will be explained below in detail in conjunction with examples.

Example 1

A reaction tube which had a inner diameter of 30 mm and a height of 300 mm and was made of SUS 316 and which was equipped with a jacket was filled with 100 ml of a commercially available macroporous type strong acid cation exchange resin Lewatit SPC-118, and there were fed from the bottom of the reaction tube, 96% propylene (the balance 4%: propane) in a flow rate of 400 mmol per hour, propane in a flow rage of 214 mmol per hour (corresponding to 60 mole based on the feed amount of propylene), and water in a flow rate of 165 mmol per hour. A liquid phase of 115 g per hour was continuously drawn out of the upper part of the reaction tube and circulated to the bottom of the reaction tube while maintaining the temperature and the pressure of the reaction tube at 130° C. and 80 atm, respectively. After the pressure of the vapor phase which was continuously discharged from the outlet of the reaction tube was reduced to 30 atm with a pressure controlling valve, the vapor phase was cooled down to 80° C. by a vapor-liquid separating tube, and the liquid phase was continuously drawn out of the bottom of the vapor-liquid separating tube. After it was confirmed that the flow rates and the temperatures of the respective parts reached steady state in 24 hours after starting this operation, measured were the flow rate and the composition of the vapor phase drawn out of the upper part of the vapor-liquid separating tube, the flow rate and the composition of the liquid phase drawn out of the bottom of the vapor-liquid separating tube, and the composition of the circulated liquid phase in the reaction tube. The concentration of isopropyl alcohol in the circulated liquid phase in the reaction tube was 2.8 mole % (8.8 weight %).

Shown in Table 1 are the flow rates and the compositions in the respective parts, and a propylene conversion between the inlet and the outlet of the reaction tube, which is calculated from the amount of propylene fed to the reaction tube and the amount of propylene in the vapor phase drawn out of the reaction tube.

Example 2

In the apparatus used in Example 1, propane was not supplied, and n-butane was fed in place of propane while maintaining a ratio of 50 mole % to propylene. The same circulated rate of the liquid phase was maintained, and the same operation was carried out. Isopropyl alcohol in the liquid phase drawn out of the vapor-liquid separating tube was analyzed from time to time and the amount of propylene fed to the reaction tube was controlled so that this flow rate of isopropyl alcohol, that is, the alcohol production rate was the same as that in Example 1. The results obtained by carrying out the same operations as those in Example 1 except the above operation are shown together in Table 1.

Comparative Example 1

In the apparatus used in Example 1, neither propane nor n-butane was fed, and only 96% propylene and water were fed to the reaction tube. The same circulated rate of the liquid phase was maintained, and the same operation was carried out. Isopropyl alcohol in the liquid phase drawn out of the vapor-liquid separating tube was analyzed from time to time, and the amount of propylene fed to the reaction tube was controlled so that the flow rate of isopropyl alcohol, that is, the alcohol production amounts was the same as that in Example 1. The results obtained by carrying out the same operations as those in Example 1 except the above operation are shown together in Table 1.

TABLE 1

Propylene conversion and alcohol concentration

|  | Example 1 | Example 2 | Comp. Ex. 1 |
|---|---|---|---|
| Flow rate to reaction tube (mmol/hour) |  |  |  |
| Propylene (1) | 384 | 266 | 943 |
| Propane | 230 | 11 | 39 |
| n-Butane | 0 | 133 | 0 |
| Total | 614 | 410 | 982 |
| Propylene flow rate (2) in vapor phase in vapor-liquid separating tube (mmol/hour) | 280 | 162 | 839 |
| Propylene conversion in reaction tube [(1) − (2)]/(1) x 100 (%) | 27 | 39 | 11 |
| Flow rate of isopropyl alcohol in liquid phase drawn out of vapor-liquid separating tube (mmol/hour) | 102 | 102 | 102 |
| Composition of liquid phase drawn out of vapor-liquid separating tube (mol %)(wt %) |  |  |  |
| Isopropyl alcohol | 67(86) | 64(85) | 61(83) |
| Diisopropyl ether | 0.7(2) | 0.6(1) | 0.6(1) |
| Water | 32.3(12) | 35.4(14) | 38.4(16) |

Comp. Ex.: Comparative Example

Example 3

The reaction tube which had a inner diameter of 30 mm and a height of 300 mm and was made of SUS 316 and which was equipped with a jacket was filled with 100 ml of the commercially available macroporous type strong acid cation exchange resin Lewatit SPC-118, and there were fed from the bottom of the reaction tube, 96% propylene (the balance 4% is propane, which is the saturated hydrocarbon) in a flow rate of 1300 mmol per hour, and water containing 18 weight % of isopropyl alcohol in a flow rate of 9.2 g per hour. A liquid phase of 315 g per hour was continuously drawn out of the upper part of the reaction tube and circulated to the bottom of the reaction tube while maintaining the temperature and the pressure of the reaction tube at 150° C. and 150 atm, respectively. After the pressure of a vapor phase which was continuously discharged from the outlet of the reaction tube was reduced to 30 atm with the pressure controlling valve, the vapor phase was cooled down to 80° C. by the vapor-liquid separating tube, and the liquid phase was continuously drawn out of the bottom of the vapor-liquid separating tube. After it was confirmed that the flow rates and the temperatures of the respective parts reached steady state in 8 hours after starting this operation, measured were the flow rate and the composition of the vapor phase drawn out of the upper part of the vapor-liquid separating tube, the flow rate and the composition of the liquid phase drawn out of the bottom of the vapor-liquid separating tube, and the composition of the circulated liquid phase in the reaction tube.

Shown in Table 2 are the flow rates and the compositions in the respective parts, and a propylene conversion between the inlet and the outlet of the reaction tube, which is calculated from the amount of propylene fed to the reaction tube and the amount of propylene in the vapor phase drawn out of the reaction tube.

Comparative Example 2

The same operation as that in Example 3 was carried out, except that the amount of isopropyl alcohol added to water which was fed to the reaction tube was controlled so that the concentration of isopropyl alcohol in the liquid phase discharged from the outlet of the reaction tube was 5 weight % and further that the amount of propylene fed to the reaction tube was controlled so that the flow rate of the liquid phase drawn out of the vapor-liquid separating tube was the same as that in Example 3. The results thereof are shown together in Table 2.

TABLE 2

|  | Example 3 | Comp. Example 2 |
|---|---|---|
| Flow rate (1) of propylene to reaction tube (mmol/hour) | 1300 | 3670 |
| Propylene flow rate (2) in vapor phase in vapor-liquid separating tube (mmol/hour) | 1080 | 3450 |
| Propylene conversion in reaction tube [(1) − (2)]/(1) x 100 (%) | 17 | 6.0 |
| Concentration of isopropyl alcohol in circulated liquid phase in reaction tube (weight %) | 17.7 | 5.0 |
| Flow rate of liquid phase drawn out of vapor-liquid separating tube (g/hour) | 16.8 | 16.8 |
| Flow rate of isopropyl alcohol in liquid phase drawn out of vapor-liquid separating tube (mmol/hour) | 220 | 220 |
| Composition of liquid phase drawn out of vapor-liquid separating tube |  |  |
| Isopropyl alcohol (weight %) | 79 | 79 |
| Diisopropyl ether (weight %) | 1 | 1 |
| Water (weight %) | 20 | 20 |

According to the present invention, in a process for producing isopropyl alcohol by a liquid phase direct hydration reaction of propylene, there have been solved various problems such as olefin conversion, an excess supply rate of olefin, and an expanded reactor volume, which have been involved in a process wherein produced isopropyl alcohol is selectively transferred into an unreacted olefin vapor phase to be collected.

Further, according to the present invention, a very high concentration alcohol aqueous solution can be prepared while maintaining the advantageous effect of a reduction in energy consumption for concentration.

What is claimed is:

1. A process for producing isopropyl alcohol by hydrating directly propylene and water in the presence of a strong acid solid catalyst, comprising:

(1) feeding continuously propylene, water in an amount of 1 to 30 moles per mole of propylene to be reacted, isopropyl alcohol to adjust the concentration of isopropyl alcohol to 6 to 30 weight % in a reaction liquid and a saturated hydrocarbon having 3 to 4 carbon atoms in an amount corresponding to 4 to 200 mole % of propylene fed, to a reactor in which said solid catalyst is filled or suspended, (2) carrying out a hydration reaction while maintaining the temperature and the pressure of the inside of the reactor in the conditions of 50° to 200° C. and 60 to 250 atm, (3) circulating at least a part of a liquid phase out of the reaction liquid to the inlet of the reactor in such a flow rate that water contained in said liquid phase accounts for at least 10 moles per mole of propylene to be reacted, and (4) drawing out a vapor phase of reaction products from the reactor together with a vapor phase of unreacted materials and the saturated hydrocarbon, liquefying isopropyl alcohol and water by reducing the pressure or cooling to separate vapor components, and refining thus obtained crude isopropyl alcohol contained in said liquefied phase to obtain refined isopropyl alcohol.

2. A process as described in claim 1, wherein the amount of the saturated hydrocarbon fed is 10 to 200 mole % based on the amount of propylene fed.

3. A process as described in claim 2, wherein the reaction temperature is 80° to 150° C.

4. A process as described in claim 2, wherein unreacted propylene and the saturated hydrocarbon are recovered from a whole amount or a part of non-condensed vapor of the vapor phase drawn out from the reactor by distillation and circulated to the inlet of the reactor.

5. A process as described in claim 1, wherein the amount of the saturated hydrocarbon fed is 10 to 100 mole % based on the amount of propylene fed.

6. A process as described in claim 5, wherein the reaction temperature is 80° to 150° C.

7. A process as described in claim 1, wherein the reaction temperature is 80° to 150° C.

8. A process described in claim 1, wherein unreacted propylene and the saturated hydrocarbon are recovered from a whole amount or a part of non-condensed vapor of the vapor phase drawn out from the reactor by distillation and circulated to the inlet of the reactor.

* * * * *